United States Patent
Kemp et al.

(10) Patent No.: US 11,752,266 B2
(45) Date of Patent: Sep. 12, 2023

(54) SYRINGE SUPPORT AND AUTOINJECTOR

(71) Applicant: Sanofi-Aventis Deutschland GMBH, Frankfurt am Main (DE)

(72) Inventors: Thomas Mark Kemp, Ashwell (GB); Louise Hodgson, Herts (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/106,278

(22) Filed: Feb. 6, 2023

(65) Prior Publication Data
US 2023/0181828 A1 Jun. 15, 2023

Related U.S. Application Data

(63) Continuation of application No. 17/738,644, filed on May 6, 2022, which is a continuation of application
(Continued)

(30) Foreign Application Priority Data

Jun. 3, 2015 (EP) .................................... 15170596

(51) Int. Cl.
*A61M 5/20* (2006.01)
*A61M 5/32* (2006.01)
*A61M 5/315* (2006.01)

(52) U.S. Cl.
CPC ...... *A61M 5/2033* (2013.01); *A61M 5/31578* (2013.01); *A61M 5/3204* (2013.01);
(Continued)

(58) Field of Classification Search
CPC .... A61M 2005/2013; A61M 2205/581; A61M 5/2033; A61M 5/3157; A61M 5/31578; A61M 5/3204
See application file for complete search history.

(56) References Cited

U.S. PATENT DOCUMENTS 6,186,980 B1 2/2001 Brunel et al.
7,597,685 B2 10/2009 Olson
(Continued)

FOREIGN PATENT DOCUMENTS

| AU | 2016269707 | 12/2020 |
|----|------------|---------|
| CH | 705345 | 2/2013 |

(Continued)

OTHER PUBLICATIONS

Amendment to the Statement of Grounds and Particulars filed in the Opposition of Australian Appln. No. 2016269707, dated Sep. 20, 2021, 25 pages.
(Continued)

*Primary Examiner* — Brandy S Lee
(74) *Attorney, Agent, or Firm* — Fish & Richardson P.C.

(57) ABSTRACT

The disclosure relates to a syringe support for supporting an axial position of a syringe relative to a housing of an autoinjector. The syringe support comprises a projecting portion, which projects from the syringe support in a distal direction and a flexible portion which axially adjoins the projecting portion. The flexible portion is adapted to axially bias the syringe in the distal direction within the housing. The disclosure further relates to an autoinjector.

30 Claims, 6 Drawing Sheets

Related U.S. Application Data

No. 17/666,696, filed on Feb. 8, 2022, now Pat. No. 11,400,216, which is a continuation of application No. 15/579,146, filed as application No. PCT/EP2016/062461 on Jun. 2, 2016, now Pat. No. 11,266,782.

(52) U.S. Cl.
CPC ... *A61M 5/3157* (2013.01); *A61M 2005/2013* (2013.01); *A61M 2205/581* (2013.01)

(56) References Cited

U.S. PATENT DOCUMENTS

| | | | |
|---|---|---|---|
| 7,771,397 | B1 | 8/2010 | Olson |
| 8,414,533 | B2 | 4/2013 | Alexandersson |
| 8,679,061 | B2 | 3/2014 | Julian et al. |
| 8,821,451 | B2 | 9/2014 | Daniel |
| 9,199,038 | B2 | 12/2015 | Daniel |
| 9,216,256 | B2 | 12/2015 | Olson et al. |
| 9,233,213 | B2 | 1/2016 | Olson et al. |
| 9,408,976 | B2 | 8/2016 | Olson et al. |
| 9,662,452 | B2 | 5/2017 | Daniel |
| 9,867,940 | B2 | 1/2018 | Holmqvist et al. |
| 10,350,356 | B2 | 7/2019 | Hirschel et al. |
| 10,376,641 | B2 | 8/2019 | Hirschel et al. |
| 10,420,898 | B2 | 9/2019 | Daniel |
| 10,434,258 | B2 | 10/2019 | Hourmand et al. |
| 10,441,719 | B2 | 10/2019 | Hourman et al. |
| 10,485,933 | B2 | 11/2019 | Vogt et al. |
| 10,569,019 | B2 | 2/2020 | Hirschel et al. |
| 10,799,647 | B2 | 10/2020 | Hostettler et al. |
| 10,881,799 | B2 | 1/2021 | Hirschel et al. |
| 11,383,044 | B2 | 7/2022 | Tschirren et al. |
| 2004/0039336 | A1 | 2/2004 | Amark et al. |
| 2004/0127857 | A1 | 7/2004 | Shemesh et al. |
| 2005/0101919 | A1 | 5/2005 | Brunnberg |
| 2007/0021718 | A1 | 1/2007 | Burren et al. |
| 2008/0262436 | A1 | 10/2008 | Olson |
| 2010/0016794 | A1 | 1/2010 | Corrigan |
| 2010/0160894 | A1* | 6/2010 | Julian ..................... A61P 19/02 434/262 |
| 2010/0249705 | A1 | 9/2010 | Kronestedt |
| 2011/0054412 | A1 | 3/2011 | Eich et al. |
| 2012/0053528 | A1 | 3/2012 | Bollenbach et al. |
| 2013/0041328 | A1 | 2/2013 | Daniel |
| 2014/0350479 | A1 | 11/2014 | Hourmand et al. |
| 2016/0008541 | A1 | 1/2016 | Hirschel et al. |
| 2016/0089498 | A1 | 3/2016 | Daniel |
| 2018/0064875 | A1 | 3/2018 | Holmqvist |
| 2018/0104414 | A1 | 4/2018 | Karlsson et al. |
| 2020/0139047 | A1 | 5/2020 | Hirschel et al. |
| 2020/0338275 | A1 | 10/2020 | Daniel |
| 2021/0154407 | A1 | 5/2021 | Hirschel et al. |
| 2023/0022361 | A1 | 1/2023 | Heiniger et al. |

FOREIGN PATENT DOCUMENTS

| | | |
|---|---|---|
| CH | 705992 | 6/2013 |
| CN | 1378468 | 11/2002 |
| CN | 101454035 | 6/2009 |
| CN | 104379195 | 2/2015 |
| EP | 1932558 | 6/2008 |
| EP | 2722066 | 4/2014 |
| EP | 2742962 | 6/2014 |
| EP | 2823841 | 1/2015 |
| EP | 2654834 | 4/2020 |
| EP | 3650064 | 5/2020 |
| EP | 3381490 | 9/2020 |
| GB | 743839 | 1/1956 |
| JP | 2009-538664 | 11/2009 |
| JP | 2013-526904 | 6/2013 |
| RU | 2010/139938 | 4/2012 |
| WO | WO 2002/047746 | 6/2002 |
| WO | WO 2005/115507 | 12/2005 |
| WO | WO 2006/057604 | 6/2006 |
| WO | WO 2007/083115 | 7/2007 |
| WO | WO 2007/138317 | 12/2007 |
| WO | WO 2009/040672 | 4/2009 |
| WO | WO 2009/094793 | 8/2009 |
| WO | WO 2010/016832 | 2/2010 |
| WO | WO 2010/017650 | 2/2010 |
| WO | WO 2010/035059 | 4/2010 |
| WO | WO 2010/043533 | 4/2010 |
| WO | WO 2010/136077 | 12/2010 |
| WO | WO 2010/136078 | 12/2010 |
| WO | WO 2010/139635 | 12/2010 |
| WO | WO 2011/005177 | 1/2011 |
| WO | WO 2011/043714 | 4/2011 |
| WO | WO 2011/123024 | 10/2011 |
| WO | WO 2012/085029 | 6/2012 |
| WO | WO 2013/016832 | 2/2013 |
| WO | WO 2013/160152 | 10/2013 |
| WO | WO 2014/060215 | 4/2014 |
| WO | WO 2014/146210 | 9/2014 |
| WO | WO 2015/015230 | 2/2015 |
| WO | WO 2016/193355 | 12/2016 |
| WO | WO 2021/008839 | 1/2021 |
| WO | WO 2021/160540 | 8/2021 |
| WO | WO 2021/197804 | 10/2021 |
| WO | WO 2022/069617 | 4/2022 |
| WO | WO 2022/184388 | 9/2022 |

OTHER PUBLICATIONS

Declaration by Antonio Farieta filed in the Opposition of Australian Appln. No. 2016269707, dated Mar. 24, 2021, 10 pages.
Declaration of Nigel David Harrison filed in the Opposition of Australian Appln. No. 2016269707, dated Dec. 22, 2021, 11 pages.
Declaration of Robert Wilson filed in the Opposition of Australian Appln. No. 2016269707, dated Dec. 21, 2021, 22 pages.
Exhibits to the Nigel David Harrison Declaration filed in the Opposition of Australian Appln. No. 2016269707, dated Dec. 22, 2021, 21 pages.
Exhibits to the Nigel David Harrison Declaration filed in the Opposition of Australian Appln. No. 2016269707, dated Jan. 17, 2022, 172 pages.
Exhibits to the Robert Wilson Declaration filed in the Opposition of Australian Appln. No. 2016269707, dated Dec. 21, 2021, 185 pages.
Second Declaration of Nigel David Harrison filed in the Opposition of Australian Appln. No. 2016269707, dated Jan. 17, 2022, 26 pages.
Statement of Grounds and Particulars filed in the Opposition of Australian Appln. No. 2016269707, dated Jun. 17, 2021, 9 pages.
EP Office Action in European Appln. No. 16726333.4, dated Aug. 23, 2019, 18 pages.
International Preliminary Report on Patentability in International Appln. No PCT/EP2016/062461, dated Dec. 5, 2017, 7 pages.
International Search Report and Written Opinion in International Appln. No. PCT/EP2016/062461, dated Aug. 17, 2016, 11 pages.
JP Opposition filed by SHL Medical in Japanese Appln. No. 2017-562766, dated Oct. 6, 2021, 97 pages (with English translation).

\* cited by examiner

SYRINGE SUPPORT AND AUTOINJECTOR

CROSS REFERENCE TO RELATED APPLICATIONS

The present application is a continuation application of U.S. patent application Ser. No. 17/738,644, filed on May 6, 2022, which is a continuation of U.S. patent application Ser. No. 17/666,696, filed on Feb. 8, 2022, which is a continuation application of U.S. patent application Ser. No. 15/579,146, filed on Dec. 1, 2017, which is the national stage entry of International Patent Application No. PCT/EP2016/062461, filed on Jun. 2, 2016, and claims priority to EP Application No. 15170596.9, filed on Jun. 3, 2015, the disclosures of which are expressly incorporated herein in entirety by reference thereto.

TECHNICAL FIELD

The disclosure relates to a syringe support and to an autoinjector.

BACKGROUND

Administering an injection is a process that presents a number of mental and physical risks and challenges for users and healthcare professionals. Injection devices typically fall into two categories—manual devices and autoinjectors. In a conventional manual device, manual force is required to drive a medicament through a needle. This is typically done by a plunger that has to be continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). Additionally, aligning the injection device, administering the injection, and keeping the injection device still during the injection may require dexterity which some patients may not have.

Autoinjector devices may be single-use or reusable devices and aim to make self-injection easier for patients. A conventional autoinjector may completely or partially replace activities involved in parenteral drug delivery from a manual device. Typically, such activities include removal of a protective syringe cap, insertion of the needle, providing the force for administering the injection and possibly removal and shielding of the used needle.

There remains a need for a syringe support within the autoinjector and an improved autoinjector comprising such a syringe support so that the autoinjector and its components, in particular a syringe, are securely arranged within a housing.

SUMMARY

One aspect of the present disclosure relates to a syringe support for supporting an axial position of a syringe relative to a housing of an autoinjector, wherein the syringe support comprises a projecting portion which projects from the syringe support into a distal direction and a flexible portion which axially adjoins the projecting portion and which is adapted to axially bias the syringe in the distal direction within the housing.

The syringe support provides a secure arrangement of the syringe within the housing. In particular, the syringe is arranged within the housing less prone to failures and damages and allows tolerance compensation. The syringe support further ensures that the syringe is biased forward against forward stop and thereby ensures that the needle is always inserted to full insertion depth. In particular, the syringe does not move backward under force of piercing skin. Furthermore, the syringe support allows that syringes with different lengths due to manufacturing tolerances may be arranged within the same housing.

In an exemplary embodiment, the flexible portion is adapted to accommodate to syringes having different lengths. In other words, the flexible portion provides a secure arrangement by compensating different syringe lengths. In particular, the flexible portion is adapted to compensate variations in length of the syringe of maximum 5%, in particular 3%. For example, the syringe support accommodates +/−1.5 mm syringe length for a syringe of 50 mm in length.

On final assembly of the syringe into a housing of an autoinjector, after the syringe has been inserted and moved to its final assembling position inside the housing, the flexible portion, also called compliant backstop, deflects axially and thus provides an axial force on the syringe to bias it forward and so prevents its axial movement during storage, transportation, drop and use. The flexible portion is sized to accommodate the tolerances of both the syringe and the autoinjector, in particular the housing, whilst limiting the movement of the syringe during drop to prevent accidental de-booting of the syringe. The stiffness of the flexible portion is tailored to provide a minimum force required to restrain the syringe during storage, transportation, drop, and use so as to not unduly stress the syringe flange and for example risk glass fracture.

In an exemplary embodiment, the flexible portion is designed in the form of a web, in the form of a flexure beam or in the form of a spring arm. Moreover, the flexible portion is of meander-shaped, accordion-shaped, labyrinth-shaped, U-shaped, V-shaped, W-shaped or S-shaped design. In particular, the flexible portion is of an accordion-shaped or labyrinth-shaped design to be maintained in a relaxed position and to form a stop for the syringe for compensating different syringe lengths. Furthermore, the flexible portion may be stressed during assembling of the syringe due to different lengths of the syringes to avoid or at least minimize risk of damages. For instance, during assembling, the syringe is carried and holds by a syringe carrier at its distal end wherein the proximal end, namely the flange, of the syringe projects the proximal end of the syringe carrier so that the flexible portion, engaging the flange, deflects and further stresses axially rearwards so that the length of the syringe can be compensated.

Furthermore, the flexible portion may be formed from resilient material. The flexible portion is designed to provide a reasonable compressive strength as well as a bending strength. In particular, the flexible portion may be formed from a corresponding resilient material, e.g. plastic, and/or with a corresponding structural design, e.g. horizontal and vertical webs and ribs. Furthermore, the projecting portion is stronger than the flexible portion, e.g. the plastic of the projecting portion is stronger than the plastic of the flexible portion.

Moreover, the resilient flexible portion could be in the form of a multiply bent arc of resilient material, wherein at least one end of the multiply bent arc is attached to the syringe support and an outer free end of the multiply bent arc is in juxtaposition with the flange of the syringe. The flexible portion axially extends in the distal direction.

In an exemplary embodiment, the flexible portion is located distally on the syringe support. Thereby, the distal flexible portion retains the syringe in position. The distal end of the distal flexible portion is a free end. The opposite proximal end of the distal flexible portion adjoins the projecting portion. Furthermore, more than one flexible portion may be arranged around the circumference of the syringe flange, thus the syringe is reliably held in position.

Moreover, the flexible portion is integrally formed with the projecting portion so that the flexible portion deflects axially rearwards against the projecting portion when the syringe is assembled or moves rearwards. In particular, the flexible portion may be integrally moulded with the syringe support for ease of manufacture, e.g. may be produced in an injection moulding die by injection moulding from plastic.

Furthermore, the syringe support may comprise a number of projecting portions with adjoined flexible portions that interact with the flange of the syringe for providing length compensation or a damping and a restricting of an axial movement of smaller syringes rearwards when the syringe is assembled and in place within the housing. Furthermore, the flexible portions may be arranged around the circumference of the syringe flange, thus the syringe is reliably held in position.

In a further embodiment, at least two flexible portions are arranged distally on the syringe support. The at least two flexible portions are arranged opposed to each other. More than two flexible portions may be provided and may be symmetrically arranged on the syringe support. The flexible portions are adapted to provide a secure axial support and positioning of the syringe relative to the housing in the rearward direction. Thus, a risk of breakage is reduced.

According to another aspect of the disclosure, an autoinjector comprises a syringe support as described above and a housing, wherein the housing comprises such a syringe support.

In an assembled state, the flexible portion and the flange of the syringe contact one another and are pressed onto one another so that the syringe is securely positioned.

In an exemplary embodiment, the flexible portion is distally attached to the projecting portion. In particular, the flexible portion is biased in the distal direction.

In an exemplary embodiment, the syringe support comprises at least two rigid projecting portions, e.g. rigid arms, wherein each rigid arm comprises one flexible portion. In particular, the two rigid arms are formed as inner arms which inwardly extend from a proximal outer housing part, e.g. a proximal end, into the housing.

In particular, the housing comprises a front part and a rear part wherein the flexible portion is arranged on the rear part. The rear part comprises a proximal end from which the rigid arms are inwardly extended. In this way, the flexible portion is arranged on a distal end of the rigid arms.

Furthermore, the housing comprises a proximal end which is larger than a proximal aperture of the housing. Thereby, the proximal end of the rear part rests on the edge of the proximal aperture of the front part to proximally close the housing.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given herein below and the accompanying drawings which are given by way of illustration only, and thus, are not limitative of the present invention.

Corresponding parts are marked with the same reference symbols in all figures.

DETAILED DESCRIPTION

Figure 1:
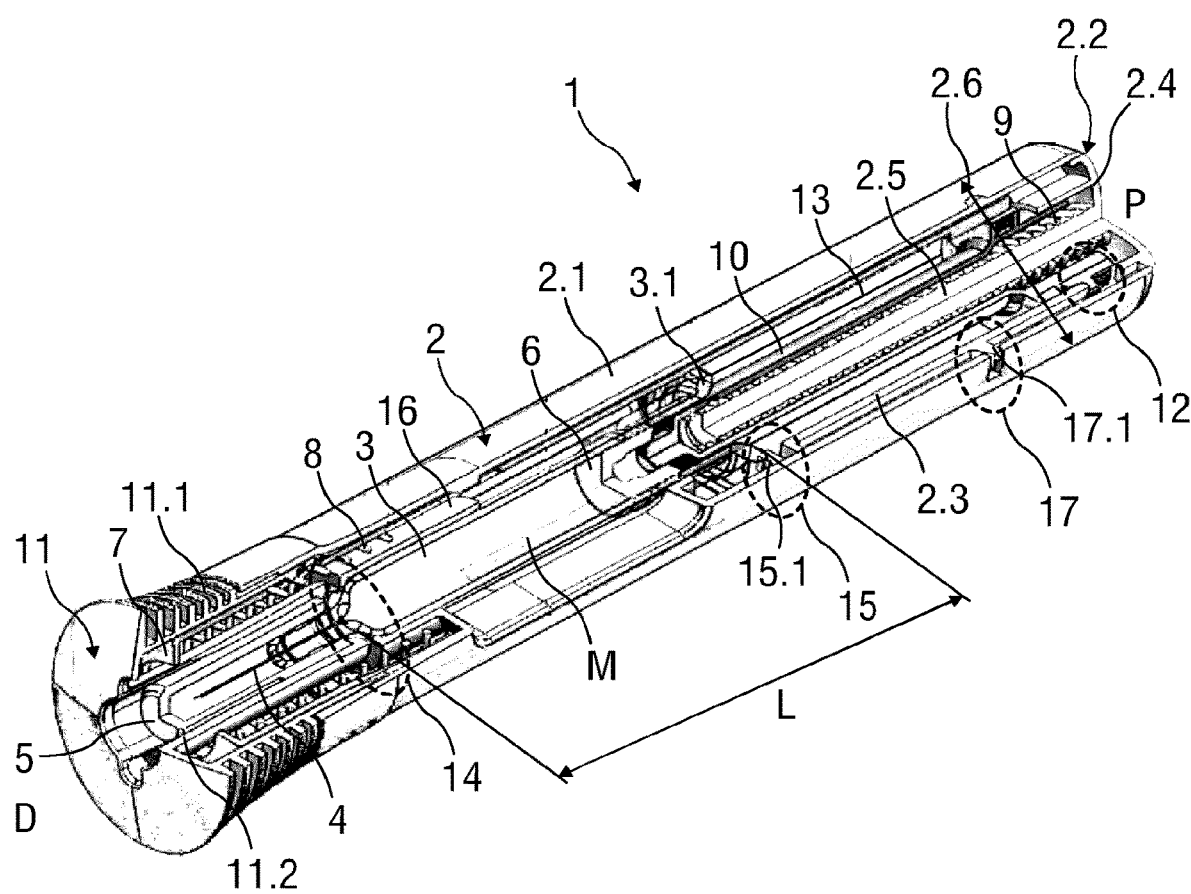
FIG. 1 is a schematic perspective partial section of an exemplary embodiment of an autoinjector.

FIG. 1 is a schematic perspective partial section of an exemplary embodiment of an autoinjector 1 in a state after assembly.

The autoinjector 1 comprises a housing 2 including a sleeve-shaped front part 2.1 and a rear part 2.2. Alternatively, the housing 2 may be formed as a one-piece housing (not shown).

The housing 2 is adapted to hold a syringe 3, e.g. a glass syringe. The syringe 3 may be a pre-filled syringe containing a liquid medicament M and have a needle 4 arranged on a distal end. In another exemplary embodiment, the syringe 3 may be a cartridge which includes the medicament M and engages a removable needle (e.g., by threads, snaps, friction, etc.). In the shown exemplary embodiment, the syringe 3 is held in the housing 2 and supported at its proximal end therein by a syringe support 15 further described below.

The autoinjector 1 further comprises a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

A stopper 6 is arranged for sealing the syringe 3 in a proximal direction P and for displacing the medicament M contained in the syringe 3 through the needle 4.

The autoinjector 1 further comprises a sleeve-shaped needle shroud 7. In an exemplary embodiment, the needle shroud 7 is telescopically coupled to the housing 2 and movable between an extended position relative to the housing 2 in which the needle 4 is covered and a retracted position relative to the housing 2 in which the needle 4 is exposed. Furthermore, a shroud spring 8 is arranged to bias the needle shroud 7 in a distal direction D against the housing 2.

A drive spring 9 in the shape of a compression spring is arranged within a proximal part of the housing 2, in particular the rear part 2.2. A plunger 10 serves for forwarding the force of the drive spring 9 to the stopper 6. In an exemplary embodiment, the plunger 10 is hollow and the drive spring 9 is arranged within the plunger 10, biasing the plunger 10 in the distal direction D against the rear part 2.2. In another exemplary embodiment, the plunger 10 may be solid and the drive 9 may engage a proximal end of the plunger 10. Likewise, the drive spring 9 could be wrapped around the outer diameter of the plunger 10 and extend within the syringe 3.

Furthermore, the autoinjector 1 comprises a cap 11 that may be removably disposed at a distal end of the housing 2, in particular at a distal end of the front part 2.1. The cap 11 may comprise grip features 11.1 for facilitating removal of the cap 11, e.g., by twisting and/or pulling the cap 11 off the case 2. The cap 11 may further include a grip element 11.2, e.g., a barb, a hook, a narrowed section, etc., arranged to engage the protective needle sheath 5, the housing 2 and/or the needle shroud 7. For example, the protective needle sheath 5 is coupled to the cap 11 in a manner that when the cap 11 is removed, the protective needle sheath 5 is also removed from the needle 4.

A plunger release mechanism 12 is arranged for preventing release of the plunger 10 prior to depression of the needle shroud 7 and for releasing the plunger 10 once the needle shroud 7 is sufficiently depressed.

In an exemplary embodiment, the autoinjector 1 further comprises at least one audible indicator 13 for producing an audible feedback for a user or patient indicating that medicament delivery is complete. In other words: The audible indicator 13 is adapted to indicate to a user or a patient that the full dose of medicament M was spent. The audible indicator 13 is formed for example as a bistable spring and is held in the rear part 2.2.

To allow an accurate support of the syringe 3 during and after assembly, the autoinjector 1 comprises a carrier 16 adapted to mount and hold the syringe 3 within the housing 2 in a forward or distal direction D.

A shroud pre-lock mechanism 14 is arranged to prevent depression of the needle shroud 7 when the cap 11 is in place, thus avoiding unintentional activation of the autoinjector 1, e.g. if dropped, during shipping or packaging, etc.

Due to manufacturing tolerance, syringes 3 may have variable lengths L. Thus, a flange 3.1 of the syringe 3 protrudes the carrier 16 in the proximal direction P. To support the axial position of the syringe 3 relative to the housing 2 after assembly, in particular during storage, transportation and normal use, the syringe support 15 comprises one or more flexible portions 15.1 axially biased to accommodate to syringes 3 having different lengths L. The flexible portions 15.1 are adapted to axially bias the syringe 3 in the distal direction D within the housing 2 and to compensate the variations in length L of the syringe 3 in the distal direction D. In particular, the syringe support 15 is adapted to accommodate the length L of the syringe 3 of maximum 5% or 3%. For example, the syringe support 15 accommodates +/−1.5 mm of the length L for a syringe 3 of 50 mm in length L.

Figure 2:
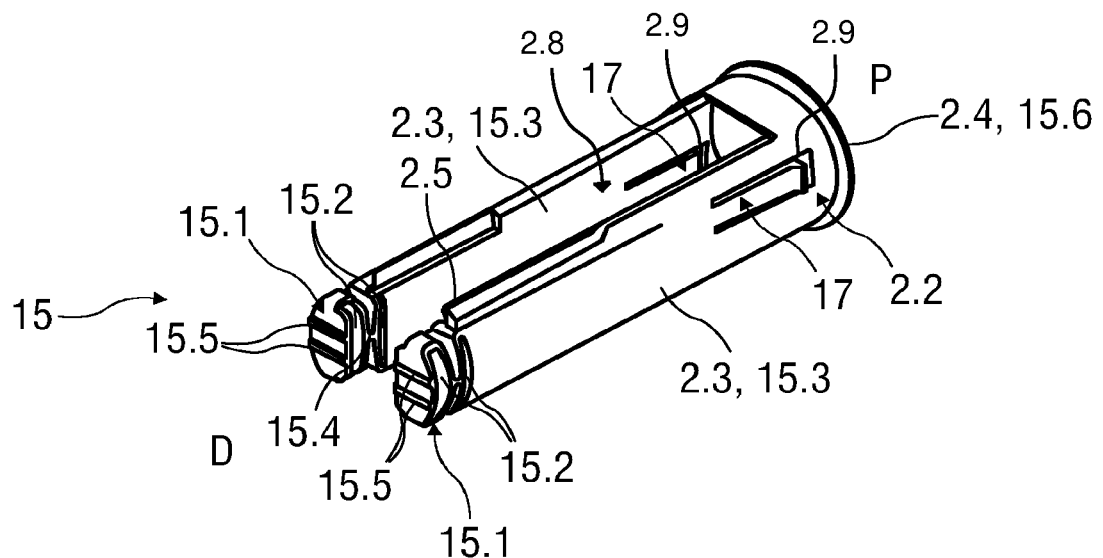
FIG. 2 is a schematic perspective view of an exemplary embodiment of a housing part comprising a syringe support from an inner end.
Figure 3:
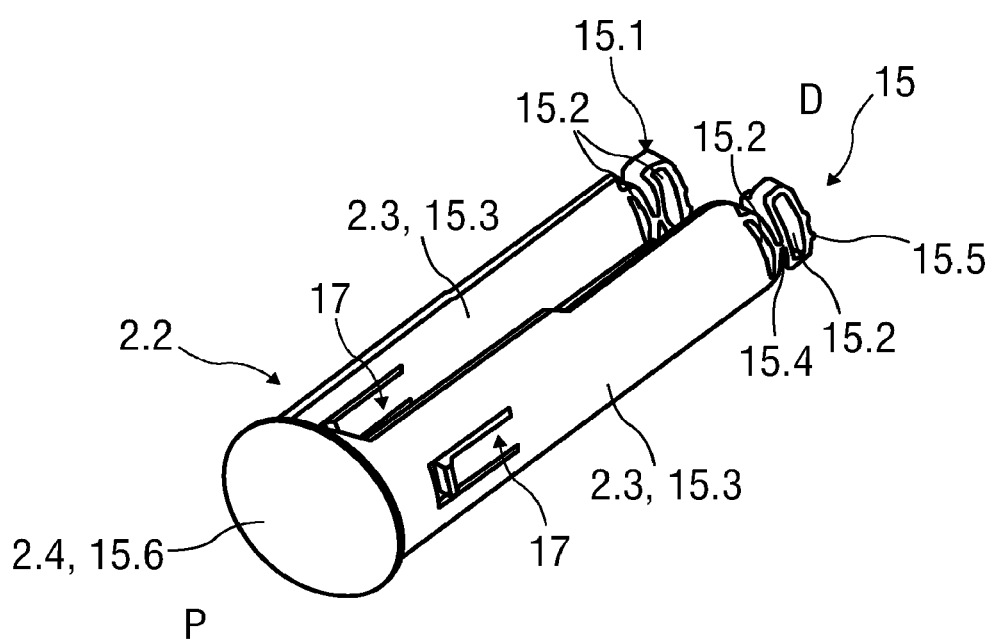
FIG. 3 is a schematic perspective view of an exemplary embodiment of a housing part comprising a syringe support from a proximal end.

FIGS. 2 and 3 are schematic views of the rear part 2.2 of the housing 2. The rear part 2.2 comprises the syringe support 15. The syringe support 15 is adapted to compensate variations in length L of the syringe 3. In detail, the syringe support 15 comprises two projecting portions 15.3 projecting in the distal direction D and, at its front or distal end, two flexible portions 15.1. The flexible portions 15.1 adjoin the projecting portions 15.3 axially in the distal direction D.

The flexible portions 15.1 are integrally formed with the projecting portions 15.3. In the shown embodiment, the projecting portions 15.3 are part of the housing 2, namely of the rear part 2.2.

The projecting portions 15.3 project from a proximal end 2.4 of the housing 2 inwardly in the distal direction D.

In the shown embodiment, the rear part 2.2 has the proximal end 2.4. The proximal end 2.4 of the rear part 2.2 is larger than a proximal aperture 2.6 so that the proximal end 2.4 rests on the edge of the proximal aperture 2.6 of the front part 2.1.

The projecting portions 15.3 of the syringe support 15 form part of the housing 2, namely two rigid arms 2.3, which are extended from the proximal end 2.4 inwards into the distal direction D. The flexible portions 15.1 are arranged on the distal end of the rear part 2.2. The rear part 2.2 includes an opening 2.8 (e.g., a third longitudinally-extending opening) between the two rigid arms 2.3.

Furthermore, the rear part 2.2 comprises a housing lock 17 having two housing lock arms 17.1 (e.g., a first deflectable arm and a second deflectable arm) to attach the rear part 2.2 to the front part 2.1. The rear part 2.2 includes two openings 2.9 (e.g., a first longitudinally-extending opening and a second longitudinally-extending opening) in which portions of the housing lock arms 17.1 are disposed. The housing lock arms 17.1 are located proximally on the syringe support 15. For secure fastening of the rear part 2.2 to the front part 2.1, the housing lock 17 has an outer diameter larger than an outer diameter of the projecting portion 15.3 in a biased state.

For assembling of the rear part 2.2 to the front part 2.1, the housing lock arms 17.1 are being deflectable inwards until they reach corresponding slots 2.7 in the front part 2.1 in which the housing lock arms 17.1 deflect outwards and latch. The housing lock arms 17.1 are arranged on a proximal section of the rear part 2.2 and are biased radially outwards.

Furthermore, the proximal end 2.4 of the rear part 2.2 forms the proximal end 15.6 of the syringe support 15 and has an outer diameter larger than an outer diameter of the projecting portion 15.3.

The flexible portions 15.1 are designed as elastic spring portions. The flexible portions 15.1 have a progressive spring characteristic curve in respect of an axial deflection such that a progressively increasing spring force in the flexible portions 15.1 occurs with increasing length L of the assembled syringe 3. Thus, the flexible portions 15.1 compensate variations in lengths L of the syringe 3 due to its axial deflection.

One end of each flexible portion 15.1 is attached to the corresponding projecting portion 15.3. The opposite distal end is a free end. The flexible portions 15.1 may be formed from resilient material, e.g. plastic.

In the shown embodiment, the flexible portions 15.1 have a labyrinth-shaped design with at least two axially arranged chambers 15.2 connected by at least one web 15.4. The distal end of the flexible portions 15.1 have at least two supporting ribs 15.5 which attach the flange 3.1 of the syringe 3 when the syringe 3 is assembled into the syringe carrier 16 and the flange 3.1 protrudes the syringe carrier 16 in the proximal direction P (see FIG. 10).

Figure 4:
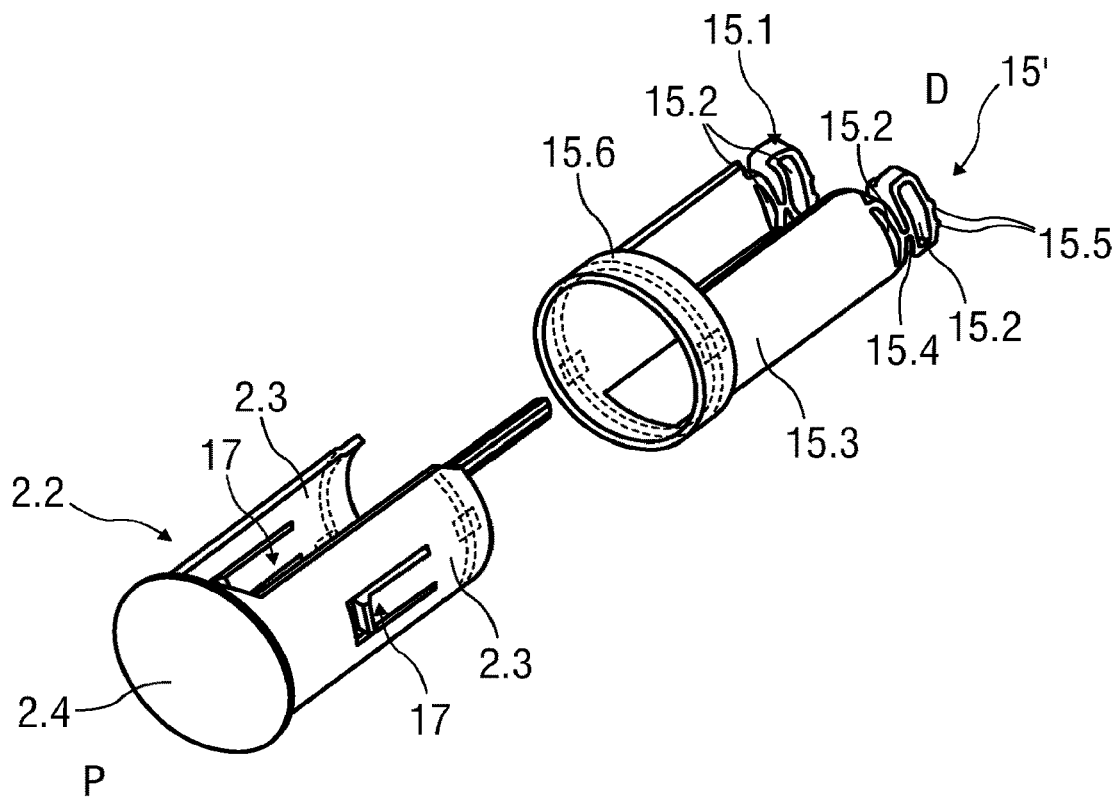
FIG. 4 is a schematic perspective view of an exemplary embodiment of a separate single syringe support and a separate single rear part.

FIG. 4 shows an alternative embodiment of a syringe support 15' formed as a separate single part and the rear part 2.2 formed as a separate single part. The syringe support 15' has a proximal support end 15.6 from which the rigid projecting portions 15.3 comprising the flexible portions 15.1 distally protrude. The proximal support end 15.6 and the housing 2, in particular the front part 2.1 or the rear part 2.2, are correspondingly adapted to retain and hold the syringe support 15' in place on the housing 2, e.g. by securing a rim in a nut or in clips on the housing 2 (shown in dotted line).

The separate rear part 2.2 only comprises the housing lock 17 for releasably connecting the rear part 2.2 with the front part 2.1 to form the housing 2.

Figure 5:
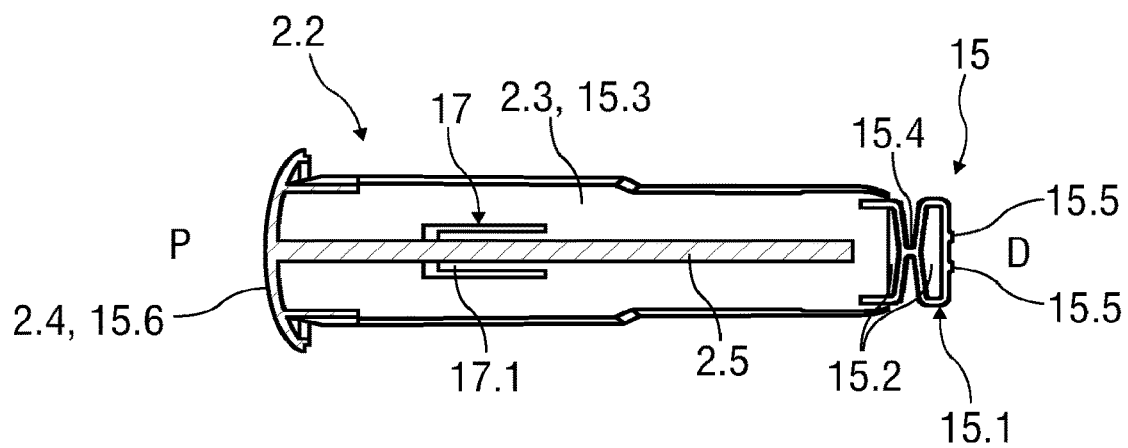
FIG. 5 is a schematic longitudinal section view of an exemplary embodiment of a housing part having a syringe support.

FIG. 5 is a schematic longitudinal section view of the rear part 2.2. The FIG. 5 shows the rear part 2.2 with one flexible portion 15.1 that are part of the syringe support 15. The flexible portion 15.1 is arranged on a distal section of the rear part 2.2 and axially biases the syringe 3 in the distal direction D.

The housing lock arms 17.1 attach the rear part 2.2 onto the front part 2.1. The housing lock arms 17.1 are proximally arranged on the rear part 2.2 and are biased radially outwards. The housing lock arms 17.1 retain the rear part 2.2 in position with the front part 2.1.

Figure 6:
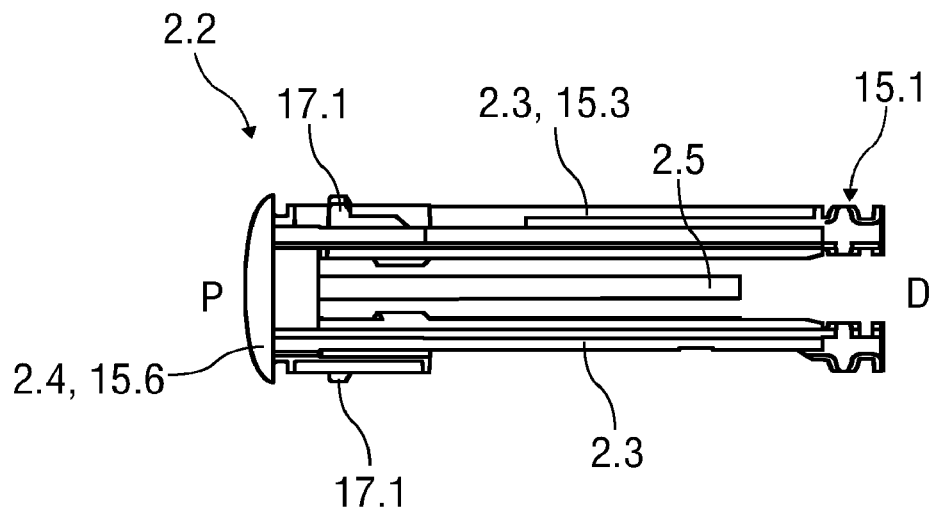
FIG. 6 is a schematic side view of a housing part having a syringe support.

FIG. 6 is a schematic side view of the rear part 2.2 comprising the syringe support 15. To guide the rear part 2.2 during assembling and to support it after assembling and during use, the rear part 2.2 comprises an inner stamp 2.5. The inner stamp 2.5 further supports the assembling and arrangement of the drive spring 9 (see FIG. 1).

Figures 7A, 7B:
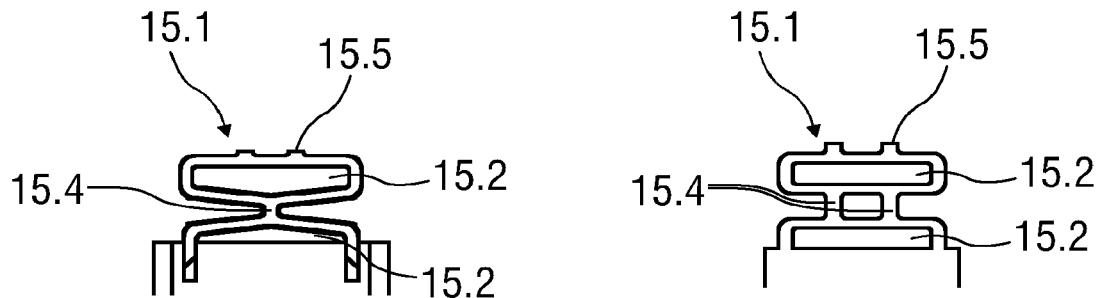
FIG. 7A to 7C is a schematic view of different exemplary embodiments of a flexible portion of a syringe support.
Figure 7C:
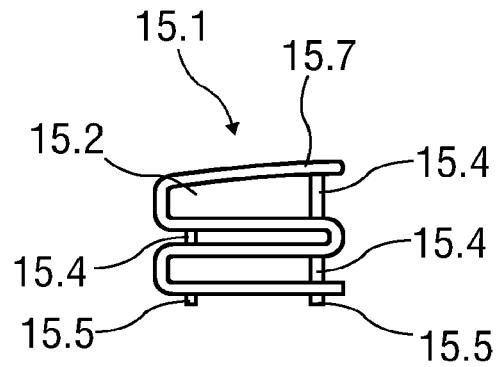

FIGS. 7A to 7C are a schematic view of different embodiments of the flexible portion 15.1 of the syringe support 15. The flexible portions 15.1 are biased axially in the distal direction D.

FIG. 7A shows a possible embodiment. The flexible portion 15.1 is designed as a bellow comprising two chambers 15.2 which are connected by two webs 15.4.

The outer surfaces of the flexible portion 15.1, namely the proximal surface attached to the projecting portion 15.3 and the distal surface of the free end, are flat.

Further at the distal flat end of the flexible portion 15.1, two ribs 15.5 are located which press against the syringe flange 3.1 in the assembled state to provide a secure axial support and positioning of the syringe 3 relative to the housing 2 in the distal direction D.

For assembling syringes 3 having variable lengths L within the same housing 2, the flexible portion 15.1 is adapted to provide an axial force on the syringe flange 3.1 and to axially bias the syringe 3 in the distal direction D. At this, the flexible portion 15.1, namely the bellow, is axially deflected and stressed so that the variable lengths L of the syringes 3 can be compensated and an axial movement of the syringe 3 is prevented during storage, transportation, drop, and use.

FIG. 7B shows an alternative embodiment of the flexible portion 15.1 designed as a bellow with one chamber 15.2 and bent webs 15.4 coupling the chamber 15.2 and the projecting portion 15.3. Supporting ribs 15.5 are attached at the distal end.

FIG. 7C shows a further embodiment of the flexible portion 15.1 of a meander-shaped form with a bent flexural beam 15.7 running in a meander-shaped manner and with connecting webs 15.4 and supporting ribs 15.5.

Furthermore, the flexible portions 15.1 may be designed in the form of a multiply folded or bent arc or half-arc, or in the form of a spring arm. Furthermore, the flexible portions 15.1 may be of an accordion-shaped, labyrinth-shaped, U-shaped, V-shaped, W-shaped, or S-shaped design.

The flexible portion 15.1 of the syringe support 15 allows compensation of length tolerances of syringes 3 to be assembled as described above.

Figure 8:
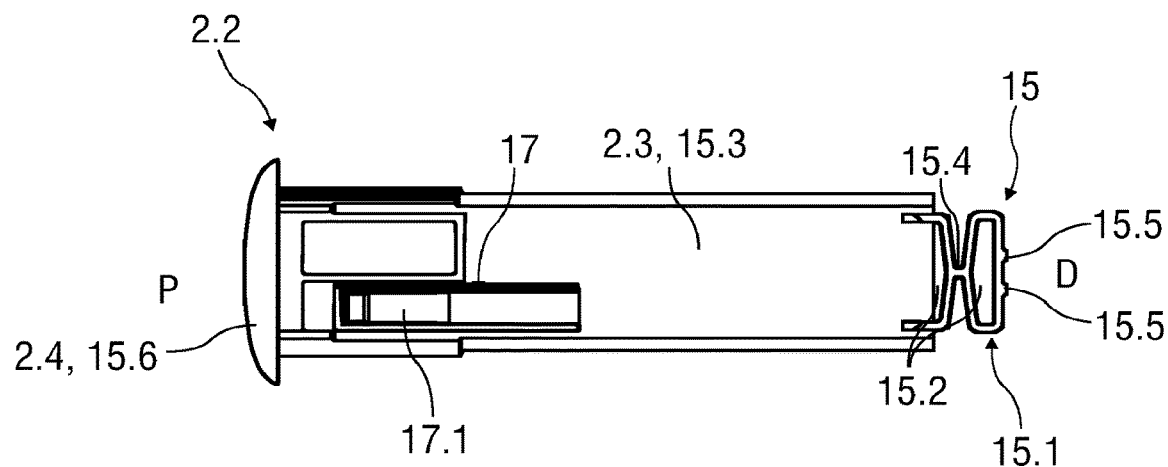
FIG. 8 is a schematic side view of an exemplary embodiment of a housing part having a syringe support.

FIG. 8 is a schematic side view of the rear part 2.2 with the flexible portion 15.1 arranged on the distal end of the rear part 2.2. The proximal end of the flexible portion 15.1 is attached to the projecting portion 15.3 and the distal end of the flexible portion 15.1 is formed as a free end axially biased.

Figure 9:
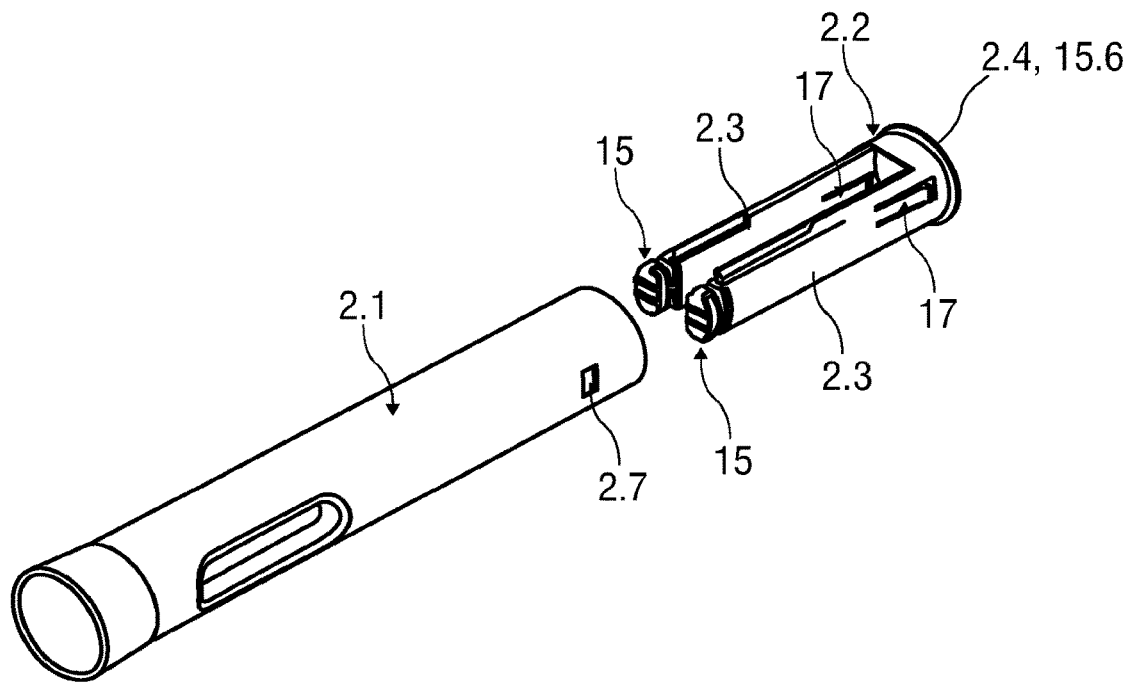
FIG. 9 is an explosion view of a rear part and a front part of a housing and FIG. 10 is a schematic perspective view of an exemplary embodiment of a syringe support and a syringe in an assembled state.

FIG. 9 shows the front part 2.1 and the rear part 2.2 of the housing 2. The front part 2.1 and the rear part 2.2 are correspondingly adapted to couple with each other, e.g. by means of a releasable connection formed by e.g. the housing locking arms 17.1 and corresponding slots 2.7.

Figure 10:
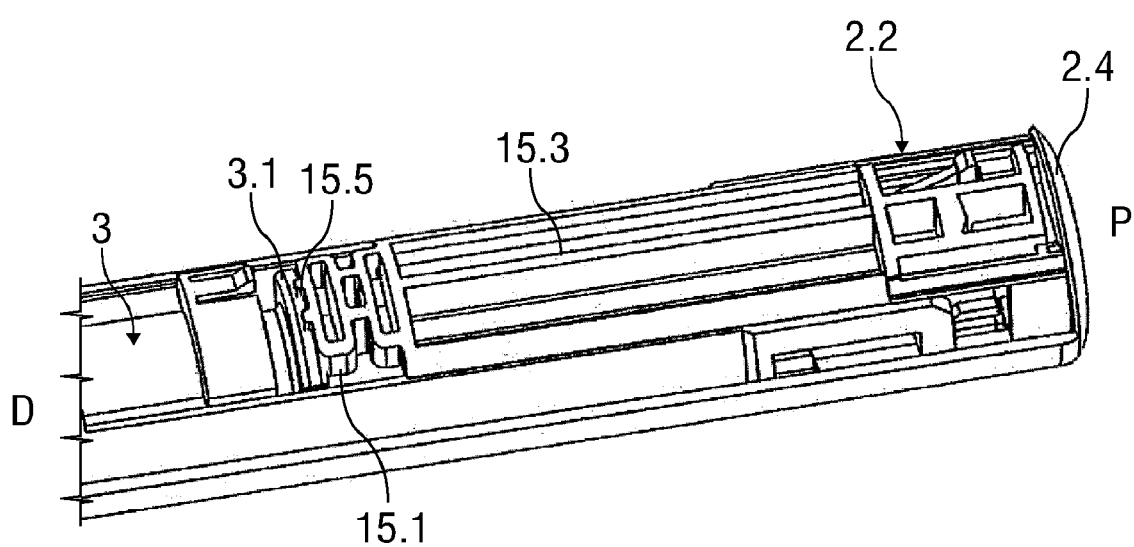

FIG. 10 shows the syringe support 15 and the syringe 3 in an assembled state. The supporting ribs 15.5 attach the flange 3.1 of the syringe 3 when the syringe 3 is assembled into the syringe carrier 16 (the syringe carrier 16 is only illustrated in FIG. 1).

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as anti sense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650 / AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

LIST OF REFERENCES 1 autoinjector
2 housing
2.1 front part
2.2 rear part
2.3 rigid arm
2.4 proximal end
2.5 stamp
2.6 proximal aperture
2.7 slot
3 syringe
3.1 flange
4 needle
5 protective needle sheath
6 stopper
7 needle shroud
8 shroud spring
9 drive spring
10 plunger
11 cap
11.1 grip feature
11.2 grip element
12 plunger release mechanism
13 audible indicator
14 shroud pre-lock mechanism
15 syringe support
15.1 flexible portion
15.2 chamber
15.3 projecting portion
15.4 web
15.5 rib
15.6 proximal support end
15.7 beam
16 carrier
17 housing lock
17.1 housing lock arm
D distal direction
L length
M medicament
P proximal direction

The invention claimed is:

1. An auto-injector comprising:
a housing;
a syringe disposed in a distal portion of the housing, the syringe comprising a proximal flange and a needle and containing a medicament;
a protective needle sheath removably coupled to the syringe to cover the needle;
a syringe carrier disposed within the housing and configured to support the syringe within the housing to limit distal movement of the syringe relative to the housing;
a sleeve-shaped needle shroud telescopically coupled to the housing and movable between an extended position in which a distal end of the sleeve-shaped needle shroud extends beyond a distal end of the needle and a retracted position in which the distal end of the needle extends beyond the distal end of the sleeve-shaped needle shroud;
a shroud spring configured to bias the sleeve-shaped needle shroud in a distal direction relative to the housing;
a syringe support coupled to a proximal portion of the housing, the syringe support comprising (i) a flexible portion disposed at a distal end of the syringe support and engaged with the proximal flange of the syringe to bias the syringe in the distal direction relative to the housing, (ii) a first longitudinally-extending opening in which a portion of a first deflectable arm of the auto-injector is disposed, (iii) a second longitudinally-extending opening located circumferentially opposite of the first longitudinally-extending opening and in which a portion of a second deflectable arm of the auto-injector is disposed, and (iv) a third longitudinally-extending opening located circumferentially between the first longitudinally-extending opening and the second longitudinally-extending opening and having a width that is greater than a width of the first longitudinally-extending opening;
a hollow plunger rod slidably disposed along a longitudinal axis of the syringe support such that the hollow plunger rod is disposed between the first longitudinally-extending opening and the second longitudinally-extending opening, the hollow plunger rod configured to move in the distal direction relative to the housing to dispense the medicament from the syringe through the needle; and
a compression drive spring disposed within the hollow plunger rod and configured to bias the hollow plunger rod in the distal direction relative to the housing.

2. The auto-injector of claim 1, wherein the width of the third longitudinally-extending opening and the width of the first longitudinally-extending opening are measured on a plane perpendicular to the longitudinal axis of the syringe support.

3. The auto-injector of claim 2, wherein the first longitudinally-extending opening and the second longitudinally-extending opening have substantially the same shape and size and the first deflectable arm and the second deflectable arm have substantially the same shape and size.

4. The auto-injector of claim 1, wherein the first longitudinally-extending opening, the second longitudinally-extending opening, and the third longitudinally-extending opening are arranged such that a plane perpendicular to the longitudinal axis of the syringe support passes through a portion of the first longitudinally-extending opening, a portion of the second longitudinally-extending opening, and a portion of the third longitudinally-extending opening.

5. The auto-injector of claim 4, wherein the plane passes through an axial center of the first longitudinally-extending opening and an axial center of the second longitudinally-extending opening.

6. The auto-injector of claim 1, wherein a proximal end of the third longitudinally-extending opening is distal to a proximal end of the first longitudinally-extending opening.

7. The auto-injector of claim 1, wherein the syringe support comprises:
  a distal portion comprising the flexible portion, the first longitudinally-extending opening, the second longitudinally-extending opening, and the third longitudinally-extending opening; and
  a proximal portion having a diameter that is greater than a diameter of the distal portion.

8. The auto-injector of claim 1, wherein the flexible portion of the syringe support is configured to maintain the engagement with the proximal flange of the syringe for syringe length variations up to 5%.

9. The auto-injector of claim 8, wherein the flexible portion of the syringe support is configured to maintain the engagement with the proximal flange of the syringe for syringe length variations between −1.5 mm and +1.5 mm.

10. The auto-injector of claim 8, wherein the syringe has a nominal axial length of 50 mm.

11. The auto-injector of claim 1, wherein the syringe support is formed of an injection-molded plastic material and the flexible portion is integrally formed with the syringe support.

12. The auto-injector of claim 1, wherein the flexible portion has a progressive spring stiffness that varies with respect to an axial deflection of the flexible portion.

13. The auto-injector of claim 12, wherein the flexible portion exerts a force on the proximal flange of the syringe in relation to a length of the syringe such that a larger force is applied to longer syringes and a smaller force is applied to shorter syringes.

14. The auto-injector of claim 1, wherein the protective needle sheath is a rigid needle sheath comprising a plastic shell.

15. The auto-injector of claim 14, comprising a cap removably attached to a distal end of the housing, the cap comprising a barb configured to engage the protective needle sheath such that removing the cap removes the protective needle sheath from the needle.

16. The auto-injector of claim 1, comprising at least one audible indicator configured to produce an audible indication after the hollow plunger rod has moved in the distal direction relative to the housing.

17. The auto-injector of claim 16, wherein the at least one audible indicator is configured to produce the audible indication when medicament delivery is substantially complete.

18. An auto-injector comprising:
  a housing;
  a syringe disposed in a distal portion of the housing, the syringe comprising a proximal flange and a needle and containing a medicament;
  a protective needle sheath removably coupled to the syringe to cover the needle;
  a syringe carrier disposed within the housing and configured to support the syringe within the housing to limit distal movement of the syringe relative to the housing;
  a syringe support coupled to a proximal portion of the housing, the syringe support comprising (i) a flexible portion disposed at a distal end of the syringe support and engaged with the proximal flange of the syringe to bias the syringe in a distal direction relative to the housing, (ii) a first longitudinally-extending opening in which a portion of a first deflectable arm of the auto-injector is disposed, (iii) a second longitudinally-extending opening located circumferentially opposite of the first longitudinally-extending opening and in which a portion of a second deflectable arm of the auto-injector is disposed, and (iv) a third longitudinally-extending opening located circumferentially between the first longitudinally-extending opening and the second longitudinally-extending opening;
  a hollow plunger rod slidably disposed along a longitudinal axis of the syringe support such that the hollow plunger rod is disposed between the first longitudinally-extending opening and the second longitudinally-extending opening, the hollow plunger rod configured to move in the distal direction relative to the housing to dispense the medicament from the syringe through the needle; and
  a compression drive spring disposed within the hollow plunger rod and configured to bias the hollow plunger rod in the distal direction relative to the housing.

19. The auto-injector of claim 18, wherein the third longitudinally-extending opening has a width that is greater than a width of the first longitudinally-extending opening.

20. The auto-injector of claim 19, wherein the width of the third longitudinally-extending opening and the width of the first longitudinally-extending opening are measured on a plane perpendicular to the longitudinal axis of the syringe support.

21. The auto-injector of claim 18, wherein the first longitudinally-extending opening, the second longitudinally-extending opening, and the third longitudinally-extending opening are arranged such that a plane perpendicular to the longitudinal axis of the syringe support passes through a portion of the first longitudinally-extending opening, a portion of the second longitudinally-extending opening, and a portion of the third longitudinally-extending opening.

22. The auto-injector of claim 21, wherein the first longitudinally-extending opening and the second longitudinally-extending opening have substantially the same shape and size, the first deflectable arm and the second deflectable arm have substantially the same shape and size, and a proximal end of the third longitudinally-extending opening is distal to a proximal end of the first longitudinally-extending opening.

23. An auto-injector comprising:
  a housing;

a syringe configured to be disposed in a distal portion of the housing, the syringe comprising a proximal flange and a needle and containing a medicament;

a syringe carrier configured to be disposed within the housing and configured to support the syringe within the housing to limit distal movement of the syringe relative to the housing; and a syringe support coupled to a proximal portion of the housing, the syringe support comprising (i) a flexible portion disposed at a distal end of the syringe support and configured to engage the proximal flange of the syringe to bias the syringe in a distal direction relative to the housing when the syringe is disposed in the distal portion of the housing, (ii) a first longitudinally-extending opening in which a portion of a first deflectable arm of the auto-injector is disposed, (iii) a second longitudinally-extending opening located circumferentially opposite of the first longitudinally-extending opening and in which a second deflectable arm of the auto-injector is disposed, and (iv) a third longitudinally-extending opening located circumferentially between the first longitudinally-extending opening and the second longitudinally-extending opening.

24. The auto-injector of claim 23, wherein the flexible portion has a progressive spring stiffness that varies with respect to an axial deflection of the flexible portion.

25. The auto-injector of claim 24, wherein the flexible portion of the syringe support is configured to maintain the engagement with the proximal flange of the syringe for syringe length variations between −1.5 mm and +1.5 mm.

26. The auto-injector of claim 23, wherein the first longitudinally-extending opening, the second longitudinally-extending opening, and the third longitudinally-extending opening are arranged such that a plane perpendicular to a longitudinal axis of the syringe support passes through a portion of the first longitudinally-extending opening, a portion of the second longitudinally-extending opening, and a portion of the third longitudinally-extending opening.

27. A method comprising:

deflecting a first deflectable arm of an auto-injector at least partially through a first longitudinally-extending opening of a syringe support of the auto-injector;

deflecting a second deflectable arm of the auto-injector at least partially through a second longitudinally-extending opening of the syringe support, the second longitudinally-extending opening located circumferentially opposite the first longitudinally-extending opening; and engaging a flexible portion of the syringe support to a proximal flange of a syringe of the auto-injector to bias the syringe in a distal direction relative to a housing of the auto-injector, the syringe and the syringe support being disposed within a distal portion of the housing, and the flexible portion being disposed at a distal end of the syringe support, wherein the syringe support comprises a third longitudinally-extending opening located circumferentially between the first longitudinally-extending opening and the second longitudinally-extending opening.

28. The method of claim 27, wherein engaging the flexible portion to the proximal flange comprises deflecting the flexible portion.

29. The method of claim 27, wherein the first longitudinally-extending opening, the second longitudinally-extending opening, and the third longitudinally-extending opening are arranged such that a plane perpendicular to a longitudinal axis of the syringe support passes through a portion of the first longitudinally-extending opening, a portion of the second longitudinally-extending opening, and a portion of the third longitudinally-extending opening.

30. The method of claim 27, comprising producing an audible indication using at least one audible indicator of the auto-injector when medicament delivery is substantially complete.

* * * * *